(12) United States Patent
Rudd et al.

(10) Patent No.: US 10,400,211 B1
(45) Date of Patent: Sep. 3, 2019

(54) CELL COMPOSITION FOR TISSUE REGENERATION

(71) Applicants: Donnie Rudd, Sugar Land, TX (US); Ramiro Contreras, Tustin, CA (US)

(72) Inventors: Donnie Rudd, Sugar Land, TX (US); Ramiro Contreras, Tustin, CA (US)

(*) Notice: Subject to any disclaimer, the term of this patent is extended or adjusted under 35 U.S.C. 154(b) by 122 days.

(21) Appl. No.: 15/466,754

(22) Filed: Mar. 22, 2017

Related U.S. Application Data

(63) Continuation-in-part of application No. 14/263,599, filed on Apr. 28, 2014.

(51) Int. Cl.
*C12N 5/074* (2010.01)
*C12N 5/073* (2010.01)
*A61K 35/51* (2015.01)

(52) U.S. Cl.
CPC ............ *C12N 5/0605* (2013.01); *A61K 35/51* (2013.01); *C12N 2502/1382* (2013.01); *C12N 2509/00* (2013.01)

(58) Field of Classification Search
CPC .......... C12N 5/0605; C12N 2502/1382; C12N 2502/025; C12N 5/0667; A61K 35/51
See application file for complete search history.

(56) References Cited

U.S. PATENT DOCUMENTS

| 7,547,546 B2 | 1/2009 | Davies et al. |
| 8,278,102 B2 | 10/2012 | Ennis et al. |
| 8,900,573 B2 | 12/2014 | Davies et al. |
| 2009/0068153 A1* | 3/2009 | Vitelli ............ A61K 35/28 424/93.7 |
| 2017/0157180 A1 | 6/2017 | Davies et al. |

FOREIGN PATENT DOCUMENTS

WO  WO2007128115  11/2007

\* cited by examiner

*Primary Examiner* — Kara D Johnson
(74) *Attorney, Agent, or Firm* — Dennis IP Law Group, LLC; W. Dennis Drehkoff

(57) ABSTRACT

A method of extracting human progenitor cells from perivascular tissue of human umbilical cord. The extracted cells are then co-cultured with nonhematopoietic stem cells and are useful to grow and repair human tissues including bone. Also included are related methods and compositions related thereto.

16 Claims, No Drawings

CELL COMPOSITION FOR TISSUE REGENERATION

This is a Continuation-In-Part application of and claims the benefit of U.S. Ser. No. 14/263,599, filed on Apr. 28, 2014, which is incorporated by reference.

FIELD OF INVENTION

This invention focuses on the harvesting of a population of rapidly proliferating human cells from the connective tissue of the umbilical cord and co-culturing these cells with adipose tissue derived stem cells.

BACKGROUND OF THE INVENTION

The obtaining of therapeutic cell mixtures from Wharton's Jelly is well known. However, in each instance it has been considered critical to insure that any trace of cord blood was eliminated, an expensive and time-consuming procedure. The present invention is not burdened with this problem. The present invention co-cultures the cells derived from Wharton's Jelly with non-hematopoietic stem cells.

The umbilical cord is one of the first structures to form following gastrulation (formation of the three embryonic germ layers). As folding is initiated, the embryonic disc becomes connected, by the primitive midgut (embryonic origin) to the primitive yolk sac (extra-embryonic origin) via the vitelline and allantoic vessels which in turn develop to form the umbilical vessels (Haynesworth et al., 1998; Pereda and Motta, 2002; Tuchmann-Duplessis et al., 1972). These vessels are supported in, and surrounded by, what is generally considered a primitive mesenchymal tissue of primarily extra-embryonic derivation called Wharton's Jelly (WJ) (Weiss, 1983). From this early stage, the umbilical cord grows, during gestation, to become the 30-50 cm cord seen at birth. It can be expected therefore, that WJ contains not only the fibroblast-like, or myo-fibroblast-like cells which have been described in the literature (see below), but also populations of progenitor cells which can give rise to the cells of the expanding volume of WJ necessary to support the growth of the cord during embryonic and fetal development.

WJ was first described by Thomas Wharton, who published his treatise Adenographia in 1656. (Wharton T W. Adenographia. Translated by Freer S. (1996). Oxford, U.K.: Oxford University Press, 1656; 242-248). It has subsequently been defined as a gelatinous, loose mucous connective tissue composed of cells dispersed in an amorphous ground substance composed of proteoglycans, including hyaluronic acid (Schoenberg et al., 1960), and different types of collagens (Nanaev et al., 1997). The cells dispersed in the matrix have been described as "fibroblast-like" that are stellate in shape in collapsed cord and elongate in distended cord (Parry, 1970). Smooth muscle cells were initially observed within the matrix (Chacko and Reynolds, 1954), although this was disputed by Parry (1970) who described them as somewhat "unusual fibroblasts" which superficially resemble smooth muscle cells. Thereafter, little work had been done on characterizing these cells until 1993 when Takechi et al. (1993) performed immunohistochemical investigations on these cells. They described the cells as "fibroblast-like" that were "fusiform or stellate in shape with long cytoplasmic processes and a wavy network of collagen fibres in an amorphous ground substance" (Takechi et al., 1993). For the immunohistochemical staining, they used primary antibodies against actin and myosin (cytoplasmic contractile proteins), vimentin (characteristic of fibroblasts of embryonic mesenchyme origin) and desmin (specific to cells of myogenic origin) in order to determine which types of myosin are associated with the WJ fibroblasts. They observed high levels of chemically extractable actomyosin; and although fibroblasts contain cytoplasmic actomyosin, they do not stain for actin or myosin, whereas the WJ fibroblasts stained positively for both. Additionally, positive stains for both vimentin and desmin were observed leading to the conclusion that these modified fibroblasts in WJ were derived from primitive mesenchymal tissue (Takechi et al., 1993). A subsequent, more recent study by Nanaev et al. (1997) demonstrated five steps of differentiation of proliferating mesenchymal progenitor cells in pre-term cords. Their findings supported the suggestion that myofibroblasts exist within the WJ matrix. The immunohistochemical characterization of the cells of WJ, shows remarkable similarities to that of pericytes which are known to be a major source of osteogenic cells in bone morphogenesis and can also form bone nodules referred to as colony forming unit-osteoblasts (CFU-O) (Aubin, 1998) in culture (Canfield et al., 2000).

Recent publications have reported methods to harvest cells from umbilical cord (UC), rather than UC blood. Mitchell et al. (Mitchell et al., 2003) describe a method in which they first remove and discard the umbilical vessels to harvest the remaining tissue. The latter, which will include both the remaining WJ (some of which will have been discarded with the vessels, since the umbilical vessels are entirely enveloped in WJ) and the amniotic epithelium, is then diced to produce small tissue fragments that are transferred to tissue culture plates. These tissue fragments are then used as primary explants from which cells migrate onto the culture substratum.

In another publication, Romanov et al. (2003) indicate they were successful in isolating mesenchymal stem cell-like cells from cord vasculature, although they also indicate their cultures do not contain cells from WJ. Specifically, they employ a single, 15 min, collagenase digestion from within the umbilical vein, which yields a mixed population of vascular endothelial and sub-endothelial cells. Romanov et al. show that sparse numbers of fibroblast-like cells appear from this cell harvest after 7 days.

It is an object of the present invention to provide a cell population comprising human progenitor cells co-cultured with hematopoetic stem cells. It is a further object of the present invention to provide human cell mixture that can be useful therapeutically.

SUMMARY OF THE INVENTION

This invention consists of:
A method of obtaining human progenitor cells comprising the steps of:
  providing a human umbilical cord with vasculature;
  washing the umbilical cord with vasculature;
  isolating the perivascular tissue proximal to the vasculature;
  digesting the perivascular tissue and thereby obtaining a soluble perivascular fraction;
  isolating human progenitor cells from the perivascular fraction; and
  co-culturing the human progenitor cells with non-hematopoietic stem cells.

More particularly, and according to one aspect of the present invention, there is provided a co-culture of Wharton's jelly extract and non-hematopoietic stem cells, wherein the extract comprises human progenitor cells and is obtained by enzymatic digestion of the Wharton's jelly proximal to the vasculature of human umbilical cord, in a region usefully termed the perivascular zone of Wharton's jelly. The tissue within this perivascular zone, and from which the present progenitor cells are extracted, can also be referred to as perivascular tissue. The extraction procedure results in an extract that is essentially free from cells of umbilical cord blood, epithelial cells or endothelial cells of the UC and cells derived from the vascular structure of the cord, where vascular structure is defined as the tunicae intima, media and adventia of arteriolar or venous vessels. The resultant extract is also distinct from other Wharton's jelly extracts isolated from the bulk Wharton's jelly tissue that has been separated from the vascular structures. These cells are then co-cultured with non-hematopoietic stem cells to create a tissue regenerating mixture.

In a related aspect, the present invention provides a cell population obtained by culturing of the cells present in the Wharton's jelly extract and then co-culturing them with non-hematopoietic stem cells. The co-culturing can be accomplished in a two-dimensional system such as t-flasks.

In one embodiment, the extracted progenitor cell population is characterized as an adherent cell population obtained following culturing of the extracted cells under adherent conditions. In another embodiment, the extracted progenitor cell population is characterized as a non-adherent (or "post-adherent") (PA) cell population present within the supernatant fraction of extracted cells grown under adherent conditions. This PA fraction is derived by transferring the supernatant of the initially plated HUCPV cells into a new T-75 flask to allow the as yet non-adhered cells to attach to the culture surface. This process is repeated with this new T-75 flask, transferring its media into another new T-75 flask in order to harvest any remaining PA cells. This PA cell population comprises, according to another aspect of the invention, a subpopulation of progenitor cells that, when cultured under adherent conditions and then co-cultured with hematopoetic stem cells, proliferates rapidly and forms bone nodules and fat cells spontaneously. This embodiment provides a means to increase the yield of adherent cells isolated from the enzymatic digest cell population.

The composition produced by this invention can be used to treat people having:
diseases resulting from a failure or dysfunction of normal blood cell production and maturation,
hyperproliferative stem cell disorders,
aplastic anemia,
pancytopenia,
thrombocytopenia,
red cell aplasia,
Blackfan-Diamond syndrome due to drugs, radiation, or infection, idiopathic;
hematopoietic malignancies,
acute lymphoblastic (lymphocytic) leukemia,
chronic lymphocytic leukemia,
acute myelogenous leukemia,
chronic myelogenous leukemia,
acute malignant myelosclerosis,
multiple myeloma,
polycythemia vera,
agnogenic myelometaplasia,
Waldenstrom's macroglobulinemia,
Hodgkin's lymphoma, non-Hodgkins's lymphoma;
immunosuppression in patients with malignant,
solid tumors, malignant melanoma, carcinoma of the stomach, ovarian carcinoma,
breast carcinoma, small cell lung, carcinoma, retinoblastoma, testicular carcinoma,
glioblastoma,
rhabdomyosarcoma,
neuroblastoma,
Ewing's sarcoma,
lymphoma;
autoimmune diseases,
rheumatoid arthritis,
diabetes type I,
chronic hepatitis,
multiple sclerosis, and systemic lupus erythematosus;
genetic (congenital) disorders,
anemias,
familial aplastic,
Fanconi's syndrome,
Bloom's syndrome, pure red cell aplasia (PRCA),
dyskeratosis congenital,
Blackfan-Diamond syndrome, congenital dyserythropoietic syndromes I-IV,
Chwachmann-Diamond syndrome,
dihydrofolate reductase deficiencies, formamino transferase deficiency,
Lesch-Nyhan syndrome,
congenital spherocytosis,
congenital elliptocytosis,
congenital stomatocytosis,
congenital Rh null disease, paroxysmal nocturnal hemoglobinuria,
G6PD (glucose-6-phosphate dehydrogenase),
variants 1,2,3, pyruvate kinase deficiency,
congenital erythropoietin sensitivity, deficiency,
sickle cell disease and trait,
thalassemia alpha, beta, gamma met-hemoglobinemia,
congenital disorders of immunity,
severe combined immunodeficiency disease, (SCID),
bare lymphocyte syndrome,
ionophore-responsive combined, immunodeficiency, combined immunodeficiency
with a capping abnormality,
nucleoside phosphorylase deficiency,
granulocyte actin deficiency,
infantile agranulocytosis,
Gaucher's disease,
adenosine deaminase deficiency,
Kostmann's syndrome, reticular dysgenesis,
congenital leukocyte dysfunction syndromes;
osteopetrosis,
myelosclerosis,
acquired hemolytic anemias,
acquired immunodeficiencies,
infectious disorders causing primary or secondary immuno-deficiencies,
bacterial infections (e.g., Brucellosis, Listerosis, tuberculosis, leprosy),
parasitic infections (e.g., malaria, Leishmaniasis),
fungal infections,
disorders involving disproportions in lymphoid cell sets and impaired immune
functions due to aging phagocyte disorders,
Kostmann's agranulocytosis,
chronic granulomatous disease,
Chediak-Higachi syndrome,
neutrophil actin deficiency,
neutrophil membrane GP-180 deficiency,
metabolic storage diseases,
mucopolysaccharidoses, mucolipidoses,
miscellaneous disorders involving immune mechanisms,
Wiskott-Aldrich Syndrome

DETAILED DESCRIPTION OF THE INVENTION

The present invention provides a co-culture of an extract of Wharton's jelly (WJ) with non-hematopoietic stem cells, as a source of a rapidly proliferating cell population comprising human progenitor cells thereby being able to repair tissue and bone.

The cells and cell populations of the present invention can be obtained by extraction from WJ of human umbilical cord and then co-cultured with non-hematopoietic stem and non-hematopoietic progenitor cells, including multipotent stromal cells, mesenchymal stem cells, tissue specific stem and non-hematopoietic progenitor cells such as liver stem cells, cardiac stem cells, human renal progenitors and neuronal progenitor cells. Mesenchymal stem cells are typically identified based upon the expression or lack of expression of particular markers. For example, MSCs are CD34−, CD11b, CD11c−, CD45−, MHC class II, CD44+, Sca-1+, and MHC class 1 low. In addition, MSCs can be identified by their ability to differentiate into various mesenchymal cells types. In vitro experiments have demonstrated that culture conditions, additives, growth factors and cytokines can precisely induce MSC to develop into selected mesenchymal cells. For example, dexamethasone in combination with isobutilmethylxanthine or insulin or a mixture of isobutilmethylxanthine, insulin and indomethacin has been shown to push the MSCs toward differentiating into adipocytes. Similarly, MSCs can differentiate into skeletal muscle cells when stimulated with 5-azacytidine. 13-VGF has been shown to cause mesenchymal stem cells to differentiate into cardiac muscle cells.

For purposes of this description, the extracted cell population portion can be referred to as human umbilical cord perivascular (HUCPV) cells. The HUCPV cell population constitutes a rich source of multipotent progenitor cells that are unique in their phenotype, particularly as revealed by the variety of cell subpopulations contained therein. Also for purposes of this description, the perivascular zone of the Wharton's jelly from which the present cells are extracted can be referred to as perivascular tissue.

As used herein, the term "progenitor cells" refers to cells that will differentiate under controlled and/or defined conditions into cells of a given phenotype. The term refers to non-hematopoietic progenitor cells. "Progenitor cells" are also characterized by the ability to self-renew in addition to differentiate. This characteristic of self-renewal is referred to "proliferation". Thus, an osteoprogenitor cell is a progenitor cell that will commit to the osteoblast lineage, and ultimately form bone tissue when cultured under conditions established for such commitment and differentiation. A progenitor cell that is "immuno-incompetent" or "non-immunogenic" is a cell having a phenotype that is negative for surface antigens associated with class I and class II major histocompatibility complexes (MHC). Such a progenitor cell is also referred to herein as an HLA double negative. A representative number of progenitor cells include: non-hematopoietic progenitor cells, endothelial progenitors, osteoprogenitor cells, liver progenitors, pancreatic progenitors, human renal progenitors and neuronal progenitor cells.

The HUCPV cell population extracted from WJ is also characterized by "rapid proliferation", which refers to the rate at which the extracted cells will grow relative to other known progenitor cell populations, under conditions that are standard for progenitor cell expansion.

The cells and cell populations of the present invention can be obtained by extraction from WJ of human umbilical cord and then co-cultured with adipose tissue derived stem cells derived from cord blood or peripheral blood. Unlike the prior art, and in accordance with the present invention, the first group of such cells are extracted from the WJ that is associated with, i.e., proximal to, the exterior wall of the umbilical vasculature. The Wharton's jelly that is associated with or very near to the external surface of the cord vasculature lies within a region termed the perivascular zone, and typically remains associated with the vasculature when the vessels are excised from the cord, as is done for instance either to extract Wharton's jelly from the cord, or to extract the vessels from the cord and associated Wharton's jelly. It has remarkably been found that the Wharton's jelly within this perivascular zone, and which has typically been discarded in prior art practice, is a rich source of progenitor cells having the characteristics herein described. Accordingly, the present invention exploits the tissue from this perivascular zone of the Wharton's jelly as a source for useful human progenitor cells, termed HUCPV cells.

As used herein the term non-hematopoietic stem cell refers to any non-blood cell forming stem cell, multipotent stromal cell or progenitor cell that can be isolated from a variety of tissues including bone marrow, adipose tissue, dental tissue, muscle tissue, bone tissue, connective tissue, neural tissue, hepatic tissue, renal tissue, bronchial tissue, gastrointestinal tissues, cardiac tissue, pancreatic tissue, placental tissue, skin tissue, and from the peripheral blood. The non-hematopoietic cells can be adipose-derived stromal cells, adipose-derived mesenchymal stem cells, liver stem cells, cardiac stem cells, neural stem cells, skin stem cells, intestinal stem cells, pancreatic stem cells, airway basal stem cells, epithelial stem cells, bile tree stem cells, dental stem cells, skeletal muscle stem cells, mammary stem cells, olfactory adult stem cells, neural crest stem cells, satellite cells, cardiac progenitor cells, endothelial progenitors, osteoprogenitor cells, liver progenitors, pancreatic progenitors, human renal progenitors and neuronal progenitor cells.

As a set of non-hematopoietic cells, human mesenchymal stem cells can be derived from a number of cell sources, for example, from placental derivatives or from bone marrow, or obtained from a number of different sources, including plugs of femoral head cancellous bone pieces, obtained from patients with degenerative joint disease during hip or knee replacement surgery, and from aspirated marrow obtained from normal donors and oncology patient who have marrow harvested for future bone marrow transplants. Although the harvested marrow is generally prepared for cell culture separation by a number of different mechanical isolation processes depending upon the source of the harvested marrow (i.e., the presence of bone chip, peripheral blood, etc.), the critical step involved in the isolation processes is the use of a specially prepared medium that contains agents that allow for not only mesenchymal stem cell growth without differentiation, but also for the direct adherence of only the mesenchymal stem cells to the plastic or glass surface area of the culture dish.

By producing a medium that allows for the selective attachment and survival of the desired mesenchymal stem cells, which are present in the marrow samples in very minute amounts, it is possible to separate the mesenchymal stem cells from the other cells (i.e., red and white blood cells, fibroblasts, other differentiated mesenchymal cells, etc.) present in the bone marrow. Other sources of human MSCs include umbilical cord, fat tissue and tooth root. MSC are multipotent progenitors for a variety of cell types of mesenchymal cell lineage, including bone, cartilage, fat, tendon, nerve tissue, fibroblasts and muscle cells. Mesenchymal stem cells can be isolated and purified form tissue such as bone marrow, blood (including peripheral blood), periosteum, and dermis, and other tissues which have mesodermal origins. In this regard, it has been found that although these progenitor cells are normally present in bone marrow, for example, in very minute amounts and that these amounts greatly decrease with age (i.e. From about $1/10,000$ cells in a relatively young patient to as few as $1/2,000,000$ in an elderly patient), human mesenchymal stem cells can be isolated from various tissues and purified when cultured in a specific medium by their selective attachment, termed "adherence" to substrates.

MSCs can be isolated from bone marrow and umbilical cord, purified and culturally expanded by any methodology acceptable in the art. Plugs or aspirates of bone marrow cells (consisting predominantly of red and white bold cells, and a very minute amount of mesenchymal stem cells) are passed through syringes to dissociate the tissue into single cells.

In one embodiment, the multipotent progenitor cells are cultured in suitable medium such as complete medium (e.g., MEM medium with 10% fetal bovine serum) and humidified atmosphere. The media is not changed for at least one day to allow the cells to attach to the culture dish. Thereafter the media is replaced every 3-4 days. When the cells have grown to confluence, the cells are detached from the culture dish, preferably with trypsin. Cells can be sub-cultured in serum-free media after removal or inactivation of the trypsin. Additional methods for isolating and culturing mesenchymal stem cells are provided in US Patent Application Nos. 20070160583 and 20070128722 are incorporated herein in their entirety. MSCs can also be isolated from Wharton's Jelly of the umbilical cord using similar methods.

In the embodiments, the HUCPV cell population is characterized by the presence of progenitor cells having many markers indicative of a functional mesenchymal (non-hematopoietic) phenotype, preferably the following markers are present on these progenitor cells including CD45−, CD34−, SH2+, SH3+, Thy-1+ and CD44+. Other preferred markers may be used to identify a functional mesenchymal phenotype as well. Preferably, the population is characterized as harboring cells that are positive for 3G5 antibody, which is a marker indicative of pericytes. The extracted cell population generally is a morphologically homogeneous fibroblastic cell population, which preferably expresses alpha-actin, desmin, and vimentin, and provides a very useful source from which desired cell subpopulations can be obtained through manipulation of culturing conditions and selection based for instance on cell sorting principles and techniques.

To extract such perivascular cells from human umbilical cord, in a preferred embodiment, care is taken during the extraction process to avoid extracting cells of the umbilical cord blood, epithelial cells or endothelial cells of the umbilical cord, and cells derived from the vascular structure of the cord, where vascular structure is defined as the tunicae intima, media and adventia of arterial or venous vessels. A preferred method of obtaining an extract that is essentially free of these unwanted cells can be achieved by careful flushing and washing of the umbilical cord prior to dissection, followed by careful dissection of the vessels from within the cord. Another preferred method is by carefully pulling the vessels away from the surrounding cord tissue in which case the perivascular tissue is excised with the vessels. It will be appreciated that, with care being taken to avoid extracting these unwanted cells, they may still be present to a small extent in the resulting extract. This is acceptable provided they occur at a frequency too low to interfere with the observed results presented herein, i.e., observation of cell colonies derived from mesenchymal and specifically mesodermal origin, frequency and rapidity of formation of CFU-F, CFU-O and CFU-A, and characterization of HLA phenotypes observed in the cultured population. It is only after the HUCPV cell population is prepared that it is co-cultured with the hematopoetic cell population.

The tissue that lies within the perivascular zone is the Wharton's jelly proximal to the external wall of the umbilical vasculature, and lies typically within a zone extending to about 3 mm from the external wall of the vessels. Preferably, the target extraction zone can lie within about 2 mm, more preferably, about 1 mm from the external wall of any one of the three vessels. The extraction of WJ from this region can be readily achieved, preferably using the technique described in the examples. In the preferred embodiments disclosed in the examples the vessels are used as a carrier for the WJ, and the vessels per se are used as the substrate from which the progenitor cells are extracted. Thus, in embodiments of the invention, cord vessels bearing a thin coating of perivascular tissue are excised either preferably surgically or more preferably manually from fresh umbilical cord that has been washed thoroughly to remove essentially all cord blood contaminants. The vessels bearing the proximal perivascular tissue, or sections thereof, are then incubated at about 37° C. in an extraction medium, preferably such as phosphate buffered saline (PBS), containing an enzyme suitable for digesting the collagen matrix of the perivascular tissue in which the desired cells reside. For this purpose, digestion with a collagenase is suitable, at a preferred concentration preferably within the range from about 0.1 mg/mL to about 10.0 mg/mL or more, more preferably 0.5 mg/mL. The enzyme type, concentration and incubation time can vary, and alternative extraction conditions can be determined readily simply by monitoring yield of cell phenotype and population under the chosen conditions. For instance, in a preferred embodiment, a higher collagenase concentration of 4 mg/mL (e.g., 1-4 mg/mL) is also suitable over a shorter digestion period of about 3 hours (e.g., 1-5 hours). During the extraction, the ends of the vessels are bound, preferably tied, or clipped, off and can be suspended above the extraction medium to avoid contamination by agents contained within the vessel. It will thus be appreciated that the present Wharton's jelly extract is essentially free from cord blood cells, umbilical cord epithelial cells, vessel endothelial cells and vessel smooth muscle cells.

Other preferred digestive enzymes and preferred concentrations that can be used in the isolation procedure are, for instance, about 0.1 to about 10 mg/ml hyaluronidase, about 0.05 to about 10 mg/ml trypsin as well as EDTA. The preferred collagenase concentration is about 4 mg/ml for a digestion period of about 3 hours, although a less expensive preferred alternative is to use about 0.5 mg/ml for about 18-24 hours. Preferably, digestion is halted at or before the vessels begins to degrade.

After about 24 hours in the preferred embodiment of about 0.5 mg/mL collagenase extraction medium, preferably 12-36 hours, and more preferably 18-24 hours, or after the preferred embodiment of about 3 hours in the about 4.0 mg/mL collagenase extraction medium, the vessels are removed, leaving a perivascular tissue extract that contains human progenitor cells. These cells are expanded under conditions standard for expansion of progenitor cells. The cells can, for instance, be selected on polystyrene to select for adherent cells, such as in polystyrene dishes or flasks and then maintained in a suitable culturing medium. In an embodiment of the invention, the extracted cells are cultured for expansion, with or without prior selection for adherent cells, under conditions of stirred suspension, as described for instance by Baksh et al in WO02/086104, the disclosure of which is incorporated herein by reference.

In a particular embodiment of the present invention, the extracted population of HUCPV cells is cultured under adherent conditions, and non-adherent cells resident in the supernatant are recovered for further culturing. Thus, in this respect, the present invention further provides an isolated population of progenitor cells extracted from perivascular tissue, the cells having the propensity to form at least one of several differentiated cell types including bone cells, cartilage cells, fat cells and muscle cells, wherein such progenitor cells constitute the non-adherent fraction of the HUCPV cells cultured under adherent conditions. Such cells are obtained by, for instance, the preferred method of culturing the perivascular tissue-extracted HUCPV cells under adherent conditions, selecting the non-adherent cell population, and then culturing the non-adherent cell population under conditions useful to (1) expand said population or (2) to cause differentiation thereof into a desired cell phenotype. It will also be appreciated that the present invention includes HUCPV subpopulations that are cultured and expanded under standard adherent culturing conditions. They are thereafter co-cultured with hematopoetic stem cells.

The cells present in the extract can, either directly or after their expansion, be sorted using established techniques to provide expandable subpopulations enriched for cells of a given phenotype. Thus, the present invention further provides perivascular tissue extracted cell populations that are enriched for multipotent mesenchymal progenitor cells, osteoprogenitor cells, cell populations that are enriched for progenitor cells, and cell populations that are enriched for multipotent and osteoprogenitor cells. Preferably, the cells can further be enriched to select for only those that are positive for the pericyte marker 3G5, using antibody thereto, and to select only for those that are negative for either one or both of the major histocompatibility complex ("MHC") class I and class II markers.

The cell populations obtained from the co-cultured extract or from a suitably enriched co-cultured fraction thereof, are useful either directly or following their expansion to provide differentiated cell populations. All of the procedures suitable for their fractionation and enrichment, and for their expansion are well established in the art, and are exemplified herein. Expansion can proceed, for instance, in the presence of factors such as IL-3 and Stem Cell Factor, and similar agents known in the art. In one embodiment, the present cell population, and particularly the osteoprogenitor cells therein, are subjected to differentiation using conditions established for the growth of bone tissue therefrom. In a preferred embodiment, a subpopulation of osteoprogenitor cells that arise from the co-culturing of the present progenitor cell population, referred to as committed osteoprogenitors, have the ability to differentiate in the absence of osteogenic supplements. Alternatively, in another preferred embodiment, the osteoprogenitor cells are cultured in a medium supplemented with one or more agents that stimulate osteogenesis, such as dexamethasone. In addition, in yet another preferred embodiment, the co-cultured cells can also be cultured with supplements suitable for stimulating differentiation into other mesenchymally-derived connective tissues (Caplan, 1991), including cartilage, muscle, tendon, adipose etc., all in accordance with standard practice in the art.

As a practical alternative to in vitro culturing of cells in the present cell population, it will be appreciated that in another preferred embodiment, the cells can be transplanted in vivo to induce the formation of a desired tissue directly within a patient.

The cells are presented in a dose effective for the intended effect. It is expected that a preferred effective cell dose will lie in the range from about $10^3$ to about $10^7$ cells, more preferably $10^4$-$10^6$ cells, and most preferably $2\times10^5$ cells, per dose. The carrier selected for delivery of those cells can vary in composition, in accordance with therapeutically acceptable and pharmaceutically acceptable procedures established for delivery of viable cells. In the embodiments, the cells are exploited for purposes of bone tissue engineering. In one embodiment, the cells are presented with a carrier in the form of a scaffold material that serves to localize the cells as an implant at a bone site that is defective or fractured, or is surgically prepared to receive the implant. A variety of materials are suitable as carriers for this purpose. In a particular embodiment, the carrier is formed of resorbable material such as calcium phosphate, PLGA or mixtures thereof. Equivalent materials can be used, provided they allow for the cells to remain viable during formation and delivery of the composition, and are otherwise physiologically compatible at the implantation site.

Still other preferred carriers suitable for delivery of the progenitor cells will include vehicles such as PBS and gels including hyaluronic acid, gelatin and the like with equivalents being useful provided they possess the pH and other properties required for cell viability.

It will also be appreciated that the present cells are useful as hosts for delivering gene expression products to the desired tissue site.

Embodiments of the invention are described in the following examples. The examples herein are for purposes of describing embodiments of the invention and are not intended to limit the invention more restrictive than that claimed.

Examples

Harvest of Progenitor Cells from Human Wharton's Jelly:

The umbilical cord is collected from full-term caesarian section infants immediately upon delivery. The umbilical cord is then transferred by the surgeon into a sterile vessel containing medium (80%.alpha.-MEM, 20% antibiotics).

All procedures from this point on are performed aseptically in a biological safety cabinet. The umbilical cord is washed in Phosphate Buffered Saline (PBS) ($-Mg^{2+}$, $-Ca^{2+}$) three times to remove as much of the umbilical cord blood as possible, and transferred back into a container with medium. A length of approximately 6 cm of cord is cut with sterile scissors and placed onto a sterile cork dissection board. The remaining cord (30-45 cm) is returned to the medium-filled container and placed into an incubator at 37° C. The 6 cm section of cord is 'twisted' against its helix, and pinned at both ends to reveal a smooth and straight surface of the umbilical cord epithelium. Using fine scissors, the umbilical cord is cut approximately 1-2 mm deep along its length to reveal the WJ. Starting with each 'flap' of cut epithelium, the WJ is teased from its inner surface using the blunt edge of a scalpel, and the teased away epithelium (approximately 0.5 mm thick) is pinned down. This procedure results in the WJ being exposed, and with its three vessels embedded in it running straight from end to end rather than helically along its longitudinal axis. Care is taken to constantly bathe the section with 37° C. PBS. Isolating one of the ends of a vessel with forceps, it is teased away from the WJ along its length until it is free of the bulk of the WJ matrix. Alternatively, the middle of the vessel can be dissected from the matrix, held with tweezers, and teased from the matrix in each direction toward its ends. Once freed by either method, the vessel is surrounded with approximately 1-2 mm of the cell-bearing WJ matrix. The dissected vessel is then clipped at both ends with either a surgical clamp, mosquito clip or sutured to create a 'loop,' blocking the passage of fluid either into or out of the vessel. The 'loop' is immediately placed along with the scissors into a 50 ml tube containing a 0.5 mg/ml collagenase solution with PBS ($-Mg^{2+}$, $-Ca^{2+}$), and placed into an incubator at 37° C. The remaining two vessels are dissected in a similar fashion, looped, and also placed in the collagenase solution in the incubator. Subsequent to the removal of the vessels, strips of WJ, constituting perivascular tissue, can easily be dissected off the epithelium and placed into 50 ml tubes with the collagenase solution. The remaining epithelial layer is then disposed of in a biohazard waste container. The same protocol is used with the remaining 30-45 cm of umbilical cord, producing 15 to 25 tubes with either 'loops' or perivascular tissue strips.

Initiation of Wharton's Jelly Progenitor Cell Cultures:

After 18-24 hours, the 'loops' are removed with the aid of their attached suspension clamp or suture and a pipette, and the remaining suspensions are then diluted 2-5 times with PBS and centrifuged at 1150 rpm for 5 minutes to obtain the cell fraction as a pellet at the bottom of the tube/s. After removal of the supernatant, the cells are resuspended in eight times volume of 4% $NH_4Cl$ for 5 minutes at room temperature in order to lyse any contaminating red blood cells. The suspensions are then centrifuged again at 1150 rpm for 5 minutes to isolate the cell fraction as a pellet, and the supernatant is removed. After counting the cells with the use of hemocytometer, they are plated directly onto T-75 $cm^2$ tissue culture polystyrene dishes, and allowed to incubate at 37° C. for 24-72 hours in order to allow the cells to attach to the polystyrene surface. The medium is then changed every two days.

The attached cells are passaged using 0.1% trypsin solution after 7 days, at which point they exhibit 80-90% confluency, as observed by light microscopy, and there is evidence of 'mineralized' aggregate formation, as revealed under phase microscopy and indicated by expected changes in optical properties. Upon passage, cells are plated either in 35 mm tissue culture polystyrene dishes or 6 well plates at $4 \times 10^3$ cells/$cm^2$ in supplemented media (SM) (75% α-MEM or D-MEM, 15% FBS, 10% antibiotics) and treated with $10^{-8}$M Dex, 5 mM β-GP and 50 .mu.g/ml ascorbic acid to test the osteogenic capacity of these cells. These plates are observed on days 2, 3, 4 and 5 of culture for CFU-O otherwise referred to as 'bone nodule' formation.

In order to test the chondrogenic capacity of these cells, $2 \times 10^5$ cells are centrifuged at 1150 rpm for 5 minutes in order to obtain the cells as a pellet. Once the supernatant is removed, the cells are maintained in SM supplemented with 10 ng/ml transforming growth factor-beta (TGF-.beta.) (and optionally with $10^{-7}$M dexamethasone). The supplemented medium is replaced every two days, maintaining the cultures for 3-5 weeks, at which point they are harvested for histology (by fixation with 10% neutral formalin buffer (NFB)), embedded in paraffin, cut into 6 .mu.m section, and stained for the presence of collagen II (antibody staining) and the presence of glycosaminoglycans (alcian blue staining). To assess the adipogenic differentiation capacity of the cells, they are initially cultured in 6-well plates in SM (with D-MEM), which is replaced every 2 days, until they reach 60% confluence. At that point the medium is replaced with the adipogenic induction medium (AIM) (88% D-MEM, 3% FBS, 33 .mu.M Biotin, 17 .mu.M Pantothenate, 5 .mu.M PPAR-gamma, 100 nM Bovine insulin, 1 .mu.M Dexamethasone, 200 .mu.M Isobutyl methylxanthine and 10% antibiotics). The AIM is replaced every 2 days for 10 days at which point the cells are fixed in 10% NFB and stained with Oil Red 0 which stains the lipid vacuoles of adipocytes red. Finally, in order to assess the myogenic capacity of the cells, they are initially cultured in T-75 cm.sup.2 tissue culture flasks in SM (with D-MEM) until they reach 80-90% confluence, at which point the medium is replaced with myogenic medium (MM) (75% D-MEM, 10% FBS, 10% Horse serum, 50 .mu.M hydrocortisone and 10% antibiotics). The MM is replaced every 2 days. After 3-5 weeks in culture, the cells are removed from the culture surface (see subculture protocol), lysed in order to obtain their mRNA, and assessed by rtPCR for the presence of several myogenic genes, including: MyoG, MyoD1, Myf5, Myosin heavy chain, myogenin and desmin Progenitor Assays Cell Proliferation Assay:

The following cell proliferation assay may be expected from the first cell culture group: During the weekly passage procedure (occurring every 6 days), aliquots of $3 \times 10^4$ cells are plated into each well of 24 6-well tissue culture polystyrene plates. On days 1, 2, 3, 4, 5 and 6 days of culture, four of the 6-well plates are passaged and the cells are counted. The exponential expansion of these cells is plotted, and the mean doubling time for the cells in these cultures is calculated. It will be noted that the doubling time for the PVWJ cell culture is about 24 hours across the entire culturing period. During the log phase, the doubling time is a remarkable 16 hours. This compares with literature reported doubling times of about 33-36 hours for bone marrow mesenchymal cells (Conget and Minguell, 1999), and about 3.2 days for mesenchymal stem cells derived from adipose tissue (Sen et al., 2001). For observation of proliferation with successive passaging, $3 \times 10^5$ cells are plated into 4 T-75 flasks (n=4) and fed with SM which is replaced every 2 days. After 6 days of culture the cells are subcultured (see sub-culture protocol above), and counted with the use of a hemocytometer. Aliquot of $3 \times 10^5$ cells are seeded into 4 new T-75 flasks, cultured for 6 days, and the process of counting is repeated. This process is repeated from P0 through P9 for 4 cord samples.

The frequency of 1:300 is significantly higher than that observed for other mesenchymal progenitor sources including neonatal BM ($1:10^4$) (Caplan, 1991), and umbilical cord blood-derived "unrestricted somatic stem cells" (USSCs) (Kogler et al., 2004) which occur at a frequency of $1:2 \times 10^8$. The initial doubling time of 60 hours at P0 drops to 38 hours at P1, which drops and maintains itself at 20 hours from P2-P8. The cells begin to enter senescence thereafter and their proliferation rate drops rapidly. Interestingly, when observed during the first 30 days of culture HUCPV cells derive $2 \times 10^{10}$ cells within 30 days. One therapeutic dose (TD) is defined as $2 \times 10^5$ cells (Horwitz et al, 1999) (Horwitz E M, Prockop D J, Fitzpatrick L A, Koo W W, Gordon P L, Neel M et al. Transplantability and therapeutic effects of bone marrow-derived mesenchymal cells in children with osteogenesis imperfecta. Nat Med 1999; 5: 309-313.).

Therefore, HUCPV cells can derive 1 TD within 10 days of culture, and 1,000 TDs within 24 days of culture.

Chondrogenic, adipogenic and myogenic differentiation of the cells can be observed.

Serial Dilution and CFU-F Assays:

Dilutions of $1\times10^5$, $5\times10^4$, $2.5\times10^4$, $1\times10^4$, $5\times10^3$, $1\times10^3$, HUCPV cells are seeded onto 6-well tissue culture plates (Falcon#353046) and fed every two days with SM. The number of colonies, comprising >16 cells, are counted in each well on day 10 of culture, and confirmed on day 14. CFU-F frequency, the average number of cells required to produce one colony, is consequently determined to be 1 CFU-F/300 HUCPV cells plated. Based on this frequency, the unit volume required to provide 300 HUCPV cells (done in triplicate from each of 3 cords) is calculated, and 8 incremental unit volumes of HUCPV cells are seeded into individual wells on 6-well plates. Again, colonies comprising >16 cells (CFU-Fs) are counted on day 10 of culture to assay CFU-F frequency with incremental seeding.

Data Analysis:

Tetracycline Stain:

Tetracycline (9 .mu.g/ml) is added to the cultures prior to termination. At termination, the cells are fixed in Karnovsky's fixative overnight and then viewed by UV-excited fluorescence imaging for tetracycline labeling of the mineral component of the nodular areas.

Scanning Electron Microscopy (SEM):

Representative samples of CFU-O cultures are prepared for SEM by first placing them in 70%, 80%, 90% and 95% ethanol for 1 hour, followed by immersion in 100% ethanol for 3 hours. They are then critical point dried. A layer of gold approximately 3 nm layer is sputter coated with a Polaron SC515 SEM Coating System onto the specimens, which are then examined at various magnifications in a Hitachi S-2000 scanning electron microscope at an accelerating voltage of 15 kV. The images generated are used to demonstrate the presence of morphologically identifiable bone matrix.

Flow Cytometry for HLA-Typing of the HUCPV Cell Population:

Test cell populations of $>1\times10^5$ cells are washed in PBS containing 2% FBS (StemCell Batch #: S13E40) and re-suspended in PBS+2% FBS with saturating concentrations (1:100 dilution) of the following conjugated mouse IgG1 HLA-A,B,C-PE and HLA-DR,DP,DQ-FITC for 30 minutes at 4° C. The cell suspension is washed twice with PBS+2% FBS, stained with 1 .mu.g/m17-AAD (BD Biosciences) and re-suspended in PBS+2% FBS for analysis on a flow cytometer (XL, Beckman-Coulter, Miami, Fla.) using the ExpoADCXL4 software (Beckman-Coulter). Positive staining is defined as the emission of a fluorescence signal that exceeded levels obtained by >99% of cells from the control population stained with matched isotype antibodies (FITC- and PE-conjugated mouse IgG1, .kappa. monoclonal isotype standards, BD Biosciences). For each sample, at least 10,000 list mode events are collected. All plots are generated in EXPO 32 ADC Analysis software.

In addition to HLA typing, the HUCPV cell population is also assessed for other markers, with the following results:

1 Marker Expression CD105 (SH2)++CD73 (SH3)++ CD90 (Thy1)++CD44++CD117 (c-kit) 15%+MHC I 75%+ MHC II–CD106 (VCAM1)–STRO1–CD123 (IL-3)–SSEA-4–Oct-4–HLA-G–CD34–CD235a (Glycophorin A)–CD45

Scanning Electron Microscopy:

The CFU-O's are observed under SEM for formation of mineralized collagen matrix which demonstrates the formation of the CFU-O's from the initial stages of collagen formation through to the densely mineralized matrix in the mature CFU-O.

Flow Cytometry & HLA-Typing of the HUCPV Cell Population:

The flow cytometry, identifying cell-surface antigens representing both Major Histocompatibility Complexes (MHCs) demonstrates 77.4% of the population of isolated cells as $MHC^{-/-}$.

The effect of freeze-thawing:

Test cell populations of $>1\times10^5$ cells are washed in PBS containing 2% FBS and re-suspended in PBS+2% FBS with saturating concentrations (1:100 dilution) of the following conjugated mouse IgG1 HLA-A,B,C-PE (BD Biosciences #555553 and CD45-Cy-Cychrome (BD Biosciences) for 30 minutes at 4° C. The cell suspension is washed twice with PBS+2% FBS and re-suspended in PBS+2% FBS for analysis on a flow cytometer (XL, Beckman-Coulter, Miami, Fla.) using the ExpoADCXL4 software (Beckman-Coulter). Positive staining is defined as the emission of a fluorescence signal that exceeded levels obtained by >99% of cells from the control population stained with matched isotype antibodies (FITC-, PE-, and Cy-cychrome-conjugated mouse IgG1, .kappa. monoclonal isotype standards, BD Biosciences), which is confirmed by positive fluorescence of human BM samples. For each sample, at least 10,000 list mode events are collected. All plots are generated in EXPO 32 ADC Analysis software.

Sub-Culture & Cell Seeding: The attached cells are sub-cultured (passaged) using 0.1% trypsin solution after 7 days, at which point they exhibit 80-90% confluency as observed by light microscopy. Upon passage, the cells are observed by flow cytometry for expression of MHC-A,B,C, MHC-DR, DP,DQ, and CD45. They are then plated in T-75 tissue culture polystyrene flasks at $4.\text{times}.10.\text{sup}.3$ cells/cm.sup.2 in SM, and treated with $10^{-8}$M Dex, 5 mM BGP and 50 .mu.g/ml ascorbic acid to test the osteogenic capacity of these cells. These flasks are observed on days 2, 3, 4, 5 and 6 of culture for CFU-O or bone nodule, formation. Any residual cells from the passaging procedure also are cryopreserved for future use.

Co-Culturing Process:

A Wharton's Jelly extract cell mixture is prepared as described above. An adipose tissue derived stem cell mixture is prepared as follows. Other stem cell mixtures are prepared similarly. Such procedures are well known in the art:

Tissue samples are obtained from patients during routine abdominoplasty. Whole intact portions of adipose tissue and associated skin are transported in sterile saline and immediately processed for cell culture.

Briefly, the adipose tissue is rinsed with PBS containing 1% penicillin and streptomycin, minced into small pieces, and then incubated in a solution containing 0.075% collagenase type IA (Sigma-Aldrich, St. Louis, Mo.) for 1 h at 37° C. with vigorous shake. The top lipid layer is removed and the remaining liquid portion is centrifuged at 220 g for 10 min at room temperature. The pellet is treated with 160 mM $NH_4Cl$ for 10 min to lyse red blood cells. The remaining cells are suspended in DMEM supplemented with 10% fetal serum, filtered through a 40-μm cell strainer (BD Biosciences, Bedford, Mass.), and plated at a density of 1 $10^6$ cells in a 10-cm dish. After reaching 80% confluence, the cells were harvested and stored in liquid nitrogen at a density of 5 $10^5$ cells per ml of freezing media (DMEM, 20% FBS, and 10% DMSO). The frozen cells were thawed for experiments as needed.

A three dimensional co-culture is initiated in the following manner. The culture device, a slow turning lateral vessel (STLV), is prepared by washing with a tissue culture detergent, (micro.x) and followed by extensive rinses and soaking in Milli Q ultra high purity water. The device is sterilized by autoclaving and upon cooling is rinsed for residuals with culture growth media. The vessel is placed in a laminar flow hood and stood upright. Cytodex 3 microcarrier beads (Pharmacia) are hydrated and sterilized before hand and suspended in a 20 mg/ml solution of growth media; each mg containing 4000 micro carriers. The vessel is filled with the growth media so that there is essentially zero headspace, which consist of minimal essential medium alpha (MEM), supplemented with insulin, transferrin, selenium, (5 ug, 10 ug, 5 ug), epidermal growth factor, sodium pyruvate, 10% serum, hepes buffer 2 grams/liter, and penicillin and streptomycin (100 units, 100 mg./ml.).

62.5 ml of a 20 mg/ml solution of microcarriers is added to the vessel to yield a final concentration of 5 mg/ml. of micro-carrier in the vessel. The vessel is then filled within 10% of the final volume with growth media. The vessel is sealed and placed in a laminar flow $CO_2$ incubator with 95% air, 5% $CO_2$, 95% humidity at 37° C. to equilibrate for one hour. At the end of one hour, the vessel is removed from the incubator and inoculated with approximately $5 \times 10^7$ cells of equal portions of the WJ mixture and adipose tissue derived cell mixture. The cells were mixed in a (9:1) ratio. After inoculation, the vessel is closed, purged of remaining air bubbles and replaced in the incubator. The vessel is equipped with a 20 ml. syringe which functions as a compliant volume. Daily monitoring of the growth in the vessel is accomplished by analysis of DCO2, DO2, glucose, mOsm and PH. At 48 hours the growth media is replaced for the first time and each 24-hours thereafter a media change is required. These changes are required to remove toxic metabolic by-products and replenish nutrient levels in the vessel. Media changes are also necessary to harvest rare growth products produced from the interaction of the multicellular organoid culture. On day 2 the rotation rate is increased from 12 to 15 RPM. At 168 hours the media composition is altered to include an additional 100 mg./dl. glucose as a result of increased consumption. At 216 hours the glucose concentration is increased to 300 mg/dl again due to the high rate of consumption. From 138 hours on the culture exhibited cell to cell organization. The culture is terminated at 288 hours to begin analysis of the well developed co-culture contained in the vessel. The growth media from the vessel is harvested and placed at −80° C. for future analysis.

The co-culturing preferably has from 25%-75% of WC cells with the remainder adipose tissue derived stem cells. Culturing with non-hematopoietic stem cells is performed similarly as known in the art as well as with specifically multipotent stromal cells, human mesenchymal stem cells, and tissue specific stem cells, adipose derived stromal cells and mesenchymal stem cells.

We claim:

1. A method of obtaining human progenitor cells comprising the steps of:
   providing a human umbilical cord with vasculature;
   washing the umbilical cord with vasculature;
   isolating perivascular tissue proximal to the vasculature;
   digesting the perivascular tissue and thereby obtaining a soluble perivascular fraction;
   isolating human progenitor cells from the perivascular fraction; and
   co-culturing the human progenitor cells with non-hematopoietic stem cells.

2. The method of claim 1 further comprising isolating the perivascular tissue from a zone extending to about 3 mm from an external wall of the umbilical cord vasculature.

3. The method of claim 2 further comprising excising perivascular tissue from the umbilical cord by pulling the vasculature fraction and the surrounding perivascular fraction away from the surrounding cord tissue.

4. The method of claim 3 further comprising tying the ends of vessels in the vasculature fraction and suspending the vessels, thereby obtaining a perivascular fraction free from cord blood cells, umbilical cord epithelial cells, vessel endothelial cells and vessel smooth muscle cells.

5. The method of claim 1 further comprising digesting the perivascular fraction with collagenase.

6. The method of claim 1 wherein the co-culturing is accomplished in a two-dimensional system.

7. The method according to claim 1 where the non-hematopoietic stem cells stem cells are selected from the group consisting of multipotent stromal cells, human mesenchymal stem cells, tissue specific stem cells.

8. The method according to claim 7 where the tissue specific stem cells are selected from the group consisting of liver stem cells, cardiac stem cells, neural stem cells, skin stem cells, intestinal stem cells, pancreatic stem cells, airway basal stem cells, epithelial stem cells, bile tree stem cells, dental stem cells, skeletal muscle stem cells, mammary stem cells, olfactory adult stem cells, neural crest stem cells, satellite cells, cardiac progenitor cells, endothelial progenitors, osteoprogenitor cells, liver progenitors, pancreatic progenitors, human renal progenitors and neuronal progenitor cells.

9. The method according to claim 1 where the non-hematopoietic stem cells are selected from the group consisting of adipose-derived stromal cells and adipose-derived mesenchymal stem cells.

10. The method according to claim 1 wherein the fraction of digested perivascular tissue is co-cultured with non-hematopoietic stem cells and non-hematopoietic progenitors cells.

11. A method of obtaining tissue regenerating cells comprising isolating a human progenitor cell from the perivascular tissue of human umbilical cord, and co-culturing said cells with non-hematopoietic stem cells.

12. A method for obtaining human progenitor cells comprising the steps of:
   providing a human umbilical cord with vasculature;
   washing the human umbilical cord with vasculature;
   isolating perivascular tissue proximal to the vasculature; and
   digesting the perivascular tissue so that human progenitor cell fractions are obtained;
   co-culturing at least a fraction of the digested perivascular tissue with non-hematopoietic stem cells to produce an expanded composition including human progenitor cells.

13. The method according to claim 12 where the non-hematopoietic are selected from the group consisting of multipotent stromal cells, human mesenchymal stem cells, tissue specific stem cells.

14. The method according to claim 13 where the tissue specific stem cells are selected from the group consisting of liver stem cells, cardiac stem cells, neural stem cells, skin stem cells, intestinal stem cells, pancreatic stem cells, airway basal stem cells, epithelial stem cells, bile tree stem cells, dental stem cells, skeletal muscle stem cells, mammary stem cells, olfactory adult stem cells, neural crest stem cells, satellite cells, cardiac progenitor cells, endothelial progenitors, osteoprogenitor cells, liver progenitors, pancreatic progenitors, human renal progenitors and neuronal progenitor cells.

16. The method according to claim 12 where the non-hematopoietic stem cells are selected from the group consisting of adipose-derived stromal cells and adipose-derived mesenchymal stem cells.

16. The method according to claim 12 wherein the fraction of digested perivascular tissue is co-cultured with non-hematopoietic stem cells and non-hematopoietic progenitors cells.

\* \* \* \* \*